United States Patent [19]

Faupel et al.

[11] Patent Number: 5,427,098
[45] Date of Patent: * Jun. 27, 1995

[54] NONINVASIVE METHOD FOR DETERMINING TREATMENT BASED UPON LESION CELL PROLIFERATION MEASUREMENTS

[75] Inventors: Mark L. Faupel, Conyers, Ga.; Mirella Merson; Virgilio Sacchini, both of Milan, Italy

[73] Assignee: Biofield Corp., Roswell, Ga.

[*] Notice: The portion of the term of this patent subsequent to Sep. 11, 2007 has been disclaimed.

[21] Appl. No.: 213,021

[22] Filed: Mar. 14, 1994

Related U.S. Application Data

[60] Continuation-in-part of Ser. No. 859,170, Mar. 27, 1992, Pat. No. 5,320,101, which is a continuation-in-part of Ser. No. 579,970, Sep. 10, 1990, Pat. No. 5,099,844, which is a division of Ser. No. 288,572, Dec. 22, 1988, Pat. No. 4,995,383.

[51] Int. Cl.⁶ .............................................. A61B 5/05
[52] U.S. Cl. ..................... 128/653.1; 128/639; 128/734
[58] Field of Search .............. 128/653.1, 630, 639, 128/733, 734, 736

[56] References Cited

U.S. PATENT DOCUMENTS

| | | | |
|---|---|---|---|
| 4,291,708 | 9/1981 | Frei et al. | 128/734 |
| 4,328,809 | 5/1982 | Hirschowitz et al. | 128/653.1 |
| 4,407,300 | 10/1983 | Davis | |
| 4,416,288 | 11/1983 | Freeman | |
| 4,486,835 | 12/1984 | Bai et al. | |
| 4,557,271 | 12/1985 | Stoller et al. | 128/639 |
| 4,557,273 | 12/1985 | Stoller et al. | 128/639 |
| 4,955,383 | 9/1990 | Faupel | 128/639 |
| 5,099,844 | 3/1992 | Faupel | 128/653.1 |
| 5,143,079 | 9/1992 | Frei et al. | 128/734 |
| 5,215,100 | 6/1993 | Spitz et al. | 128/639 |
| 5,320,101 | 6/1994 | Faupel et al. | 128/653.1 |

Primary Examiner—Krista M. Pfaffle
Attorney, Agent, or Firm—Sixbey, Friedman, Leedom & Ferguson

[57] ABSTRACT

A method for measuring biopotentials at a lesion site on a human or animal subject and determining therefrom the magnitude of cell proliferation at such lesion site. A value indicative of the cell proliferation rate is compared with one or more reference values and treatment of the lesion is made in accordance with the results of this comparison. Treatment may be automatically controlled in response to the comparison, and the efficacy of treatment is monitored by comparing values obtained from biopotentials taken before treatment with those obtained during and/or after treatment.

7 Claims, 2 Drawing Sheets

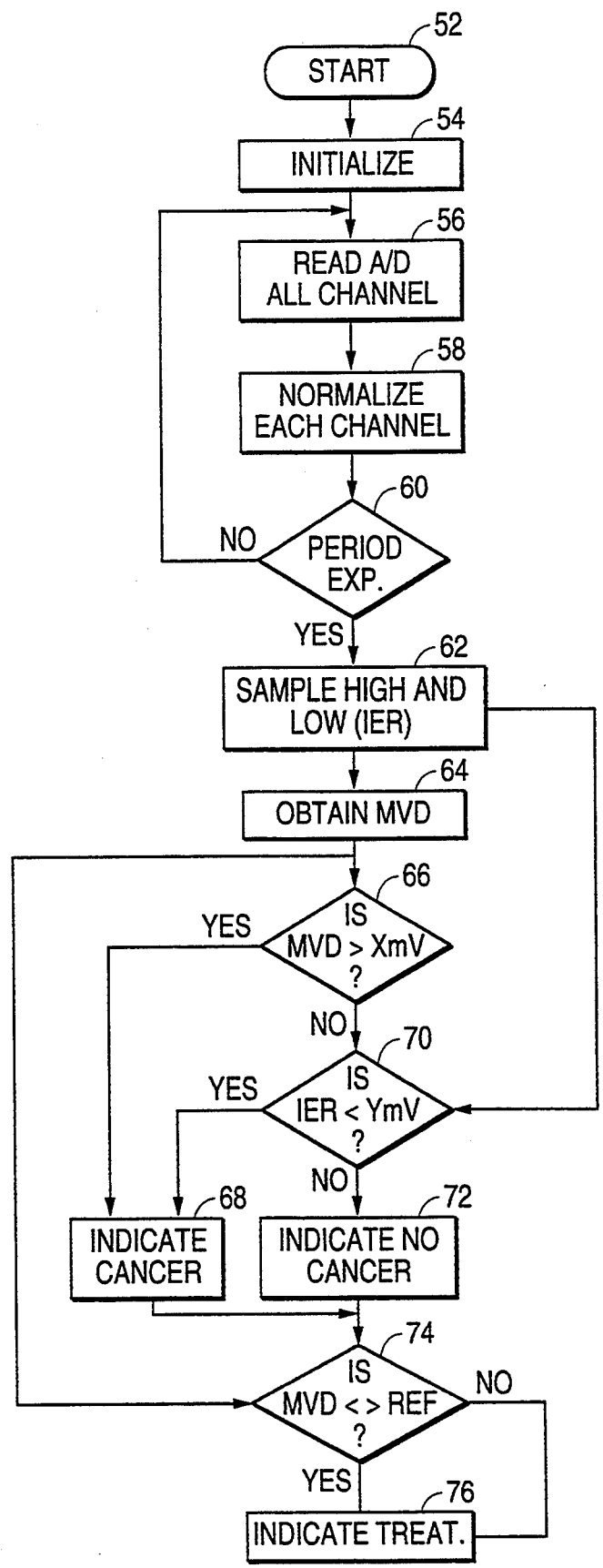

NONINVASIVE METHOD FOR DETERMINING TREATMENT BASED UPON LESION CELL PROLIFERATION MEASUREMENTS

This application is a continuation-in-part application of Ser. No. 07/859,170 filed Mar. 27, 1992, now U.S. Pat. No. 5,320,101, which is a continuation-in-part application of Ser. No. 07/579,970, filed Sep. 10, 1990, now U.S. Pat. No. 5,099,844, which is a divisional application of Ser. No. 07/288,572 filed Dec. 22, 1988, now U.S. Pat. No. 4,995,383.

TECHNICAL FIELD

The present invention relates generally to a noninvasive method for sensing the existence of a cancerous or benign lesion in a living organism by detecting the DC potential of the electromagnetic field present between a reference and a plurality of test points on the living organism. The method further includes determining the necessity for, the type and the intensity of treatment based upon a measurement of the gradient of electrical activity which occurs as a function of biological activity.

BACKGROUND ART

In recent years the theory that measurement of the potential level of the electromagnetic field of a living organism can be used as an accurate screening and diagnostic tool is gaining greater acceptance. Many methods and devices have been developed in an attempt to implement this theory. For example, U.S. Pat. No. 4,328,809 to B. H. Hirschowitz et al. deals with a device and method for detecting the potential level of the electromagnetic field present between a reference point and a test point of a living organism. Here, a reference electrode provides a first DC signal indicative of the potential level of the electromagnetic field at the reference point, while a test electrode provides a second DC signal indicative of the potential level of the electromagnetic field at the test point. These signals are provided to an analog-to-digital converter which generates a digital signal as a function of the potential difference between the two, and a processor provides an output signal indicative of a parameter or parameters of the living organism as a function of this digital signal.

Similar biopotential measuring devices are shown by U.S. Pat. Nos. 4,407,300 to Davis, and 4,557,271 and 4,557,273 to Stroller et al. Davis, in particular, discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al. patent contemplates the use of a plurality of test electrodes, while U.S. Pat. Nos. 4,416,288 to Freeman and 4,486,835 to Bai disclose the use of measuring electrode arrays.

Previous methods for employing biopotentials measured at the surface of a living organism have been used only as a diagnostic tool, and while basically valid, are predicated upon an overly simplistic hypothesis which does not provide even an effective diagnosis for many disease states. These known methods have no application in determining the treatment for a sensed disease condition.

Prior DC biopotential sensing methods and devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to diagnosis inaccuracy, particularly where only surface measurements are taken.

First, the polarity of diseased tissue underlying a recording electrode has been found to change over time. This fact results in a potential change which confounds reliable diagnosis when only one external recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

As disease states such as cancer progress, they produce local effects which include changes in vascularization, water content, and cell division rate. These effects alter ionic concentrations which can be measured at the skin surface and within the neoplastic tissues. Other local effects, such as distortions in biologically closed electrical circuits, may occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). Once this fact is recognized, it follows that important electrical indications of disease are going to be seen in the relative voltages recorded from a number of sites at and near a diseased area, and not, as previously assumed, on the direction (positive vs. negative) of polarity.

At present, once a possible lesion site has been identified and a biopsy has been taken, a prognostic method (Labeling Index) may be performed which involves examining during a biopsy the cells from a mass lesion in order to determine the cell proliferation rate for the lesion. As the Labeling Index increases, a more aggressive cancer is indicated and treatment is determined accordingly.

The problem with this Labeling Index prognostic method is that it requires a biopsy, and this invasive technique is often not practical to use in monitoring the progress of a benign lesion which may ultimately become cancerous.

DISCLOSURE OF THE INVENTION

It is a primary object of the present invention to provide a novel and improved noninvasive method for making lesion cell proliferation measurements which employs the measurement and analysis of DC biopotentials taken from the area of a lesion site on a living organism and using such measurements to control the efficacy of a treatment for the disease.

A further object of the present invention is to provide a novel and improved noninvasive method wherein DC biopotentials are received from a plurality of sites at and near a lesion area on a living organism. A maximum potential differential is then obtained from the averages of multiple biopotential values taken over time and compared with reference values to determine whether cell proliferation indicated by the level of the maximum potential differential is indicative of an aggressive cancer.

Yet a further object of the present invention is to provide a novel and improved noninvasive method for monitoring patients with benign lesions wherein DC biopotentials are received from a plurality of measuring electrodes located on the skin of a subject in the area of a suspected disease site. A maximum potential differential is then obtained from the averages of multiple biopotential values taken over time, and this maximum potential differential is compared with those previously taken to provide a true risk marker which will allow increased monitoring of high risk patients.

BRIEF DESCRIPTION OF THE DRAWINGS

FIG. 2 is a flow diagram of the measurement operation of the apparatus of FIG. 1.

BEST MODE FOR CARRYING OUT THE INVENTION

Figure 1:
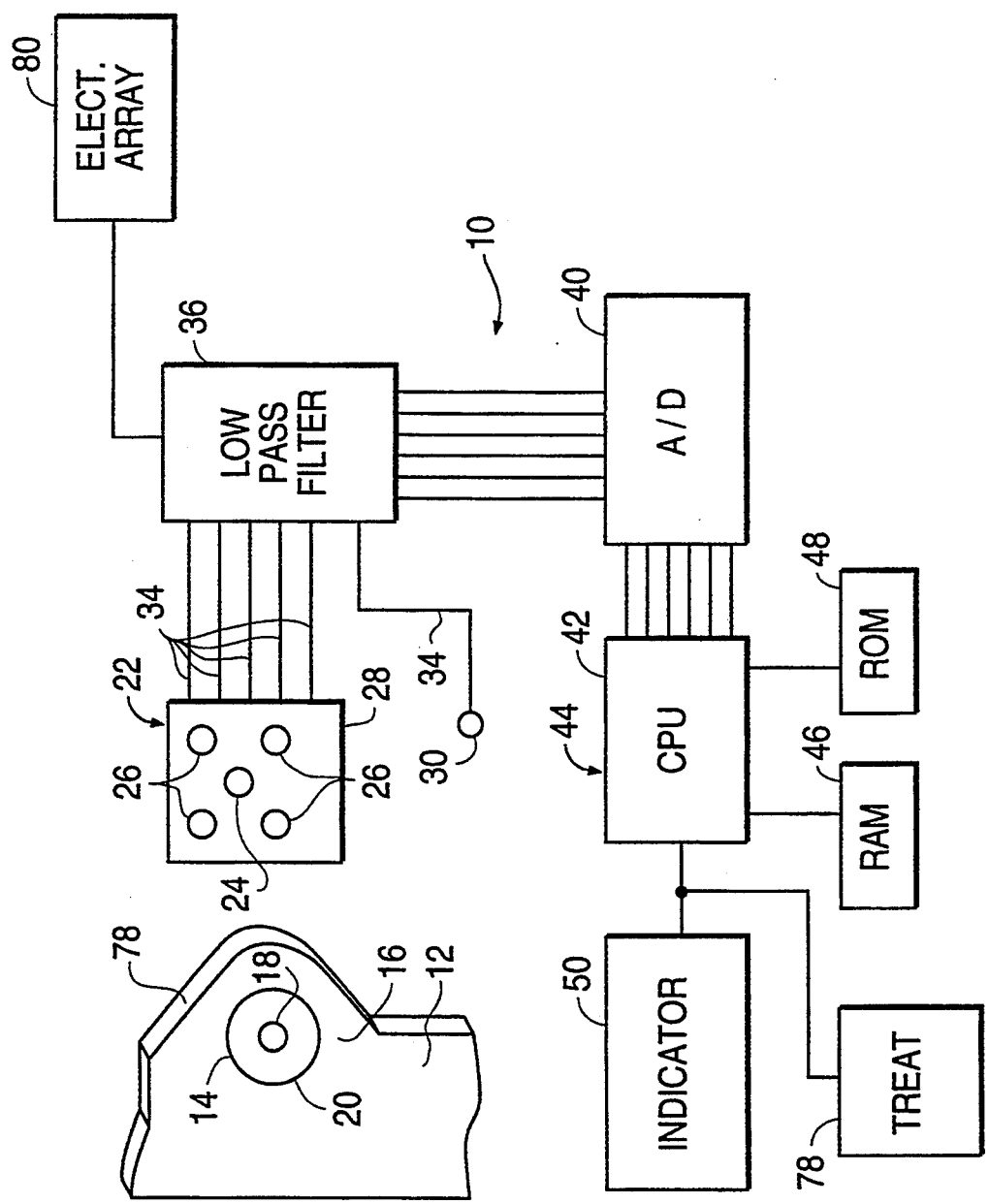
FIG. 1 is a block diagram of the apparatus used to perform the method of the present invention.

FIG. 1 discloses a basic block diagram of the apparatus indicated generally at 10 for performing a discriminant analysis to obtain a differential signal indicative of the presence or absence of a lesion, the benign or malignant state of the lesion and the cell proliferation rate of the lesion.

In FIG. 1, a human subject 12 may have a lesion 14 on one breast 16. This lesion has a core 18 and an outer zone 20 surrounding the core where various differing local effects, such as changes in vascularization, water content and cell division rate occur. The outer zone 20 will include normal cells surrounding the lesion, for these cells often exhibit a much greater biopotential effect in response to tumor growth than does the actual tumor. Assuming first, for purposes of discussion, that the location of the lesion 14 is known, and the device 10 is to be used to determine whether or not a malignant condition exists, skin surface potentials will be measured in an area of the breast, including the zone 20 using an electrode array 22. The method of this invention contemplate the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. The aim is to measure the gradient of electrical activity which occurs as a function of the underlying biological activity of the organ system. The number of electrodes used in the measurement will also be a function of the specific application.

The electrodes 24 of the electrode array 22 should be mounted in a manner which permits the electrodes to be accurately positioned against the curved surface of the breast 16 while still maintaining uniform spacing and the position of the electrodes in a predetermined pattern. The electrode array 22 is used in conjunction with a reference electrode 30, and all of these electrodes may be of a known type used for detecting the potential level of the electromagnetic field present in a living organism. Ideally, the electrodes 24 and 30 should be of a type which do not cause a substantial battery effect between the organism under test and the electrode. A common electrode suitable for use as the electrodes 24 and 30 includes a layer of silver having an electrical lead secured in electrical contact therewith. In contact with the silver layer is a layer of silver chloride, and extending in contact with the silver chloride layer is a layer of conductive electrolyte gel material which contacts the surface of a living organism. This gel can be in substantially a liquid gel form or can be impregnated in a sponge foam holder and gels with a high electrolyte concentration are preferable.

The device 10 is a multi-channel device having electrode leads 34 extending separately from the electrodes 24 and the reference electrode 30 to a low pass filter 36. This filter operates to remove undesirable high frequency AC components which appear on the slowly varying DC voltage signal outputs provided by each of the electrodes as a result of the electromagnetic field measurement. The low pass filter 36 may constitute one or more multiple input low pass filters of known type which separately filter the signals on each of the input leads 34 and then pass each of these filtered signals in a separate channel to a multiple input analog-to-digital converter 40. Obviously, the low pass filter 36 could constitute an individual low pass filter for each of the specific channels represented by the leads 34 which would provide a filtering action for only that channel, and then each filtered output signal would be connected to the input of the analog-to-digital converter 40.

The converter 40 is a multiple input multiplex analog-to-digital converter of a known type, such as that manufactured by National Semiconductor, Inc. and designated as ADC808. For multiple channels, it is possible that more than one multiple input analog-to-digital converter will be used as the converter 40. For example, if an 8-input analog-to-digital converter is used and there are 24 input and output channels from the low pass filter 36, then the analog-to-digital converter 40 might include three 8-input converters.

The analog-to-digital converter 40 converts the analog signal in each input channel to a digital signal which is provided on a separate output channel to the multiple inputs of a central processing unit 42. The central processing unit is a component of a central control unit indicated generally at 44 which includes RAM and ROM memories 46 and 48. Digital input data from the analog-to-digital converter 40 is stored in memory and is processed by the CPU in accordance with a stored program to perform the diagnostic and scanning methods of the present invention.

The operation of the discriminant analysis device 10 will be clearly understood from a brief consideration of the broad method steps of the invention which the device is intended to perform. When the lesion 14 has not been located, an electrode array 22 is positioned in place on the lesion site with the electrodes 24 positioned over various diverse areas of the site. The reference electrode 30 is then brought into contact with the skin of the subject 12 in spaced relationship to the electrode array 22, and this reference electrode might, for example, be brought into contact with a hand of the subject. Then, the electromagnetic field between the reference electrode and each of the electrodes 24 is measured, converted to a digital signal and stored for processing by the central processing unit 42. The program control for the central processing unit causes a plurality of these measurements to be taken over a period of time, and the measurements on all channels may be taken simultaneously and repetitively for the predetermined measurement time period. Alternatively, sequential measurements between the reference electrode and one of the electrodes 24 can be taken until each channel is sampled, and then the sequential measurement is repeated for the predetermined measurement period. In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the central processing unit 42 at the end of the measurement period. For the duration of a single predetermined measurement period, for example, from sixteen measurement channels, the central processor will obtain sixteen average signals indicative of the average electromagnetic field for the period between the reference electrode 30 and each of the electrodes in the electrode array 22. Of course, more reference electrodes can be used, although only one reference electrode 30 has been shown for purposes of illustration.

Having once obtained an average signal level indication for each channel, the results of the measurements taken at multiple sites are analyzed in terms of a mathematical analysis to determine the relationships between the average signal values obtained. It has been found that the result of such an analysis is that a subset of relationships can be obtained which are indicative of the presence of more serious disease, while a different subset might be obtained which will be indicative of the absence of serious disease.

The most important relationship to be obtained is designated the maximum voltage differential (MVD), which is defined as the minimum average voltage value obtained during the measurement period subtracted from the maximum average voltage value obtained for the same period where two or more electrodes are recording DC potentials from a lesion. Thus, for each predetermined measurement period, the lowest average voltage level indication obtained on any of the channels is subtracted from the highest average voltage level indication obtained on any of the channels to obtain an MVD voltage level. If this MVD voltage level is above a desired level >x, then a disease condition, such as a malignancy, could be indicated. Similarly, if the average taken over the measurement period from one channel is an abnormally low value <y, the presence of this abnormally low individual electrode reading (IER) could be indicative of a disease condition such as malignancy. These primary indicators may be further analyzed to reduce the number of false positive diagnosis, usually cases of non-malignant hyperplasia which may be falsely identified as cancer on the basis of high MVD or low IER readings.

The general overall operation of the central processing unit 42 will best be understood with reference to the flow diagram of FIG. 2. The operation of the unit 10 is started by a suitable start switch as indicated at 52 to energize the central processing unit 42, and this triggers an initiate state 54. In the initiate state, the various components of the device 10 are automatically brought to an operating mode, with for example, the indicator 50 being activated while various control registers for the central processing unit are reset to a desired state. Subsequently, at 56, a predetermined multiple measurement period is initiated and the digital outputs which are either generated in the processing unit 42 or those from the analog-to-digital converter 40 are read. The central processing unit may be programmed to simultaneously read all channel outputs or these channel outputs may be sequentially read.

Once the signals from all channels are read, an average signal for each channel is obtained at 58 for that portion of the measurement period which has expired. The average or normalized value for each channel is obtained by summing the values obtained for that channel during the measurement period and dividing the sum by the number of measurements taken. Then, at 60, the central processing unit determines whether the measurement period has expired and the desired number of measurements have been taken, and if not, the collection of measurement samples or values continues.

Once the measurement period has expired, the microprocessor will have obtained a final average value for each channel derived from the measurements taken during the span of the measurement period. From these average values, the highest and lowest average values obtained during the measurement period are sampled at 62, and at 64, and the lowest average channel value which was sampled at 62 is subtracted from the highest average channel value to obtain a maximum voltage differential value.

The maximum voltage differential value may be analyzed at 66 to determine if the value is greater than a predetermined level x (mV). If the maximum voltage differential is above the predetermined level, the existence of a disease condition is indicated at 68, but if it is not, then the lowest average channel output IER from 62 is analyzed at 70 to determine if this value is lower than a predetermined value y (mV). If it is determined at 70 that the IER value is not lower than the predetermined value, then no disease condition is indicated at 72. On the other hand, if the IER value is lower than the predetermined value, then the presence of a disease condition is indicated at 68. After the indication of the presence or nonpresence of disease at 68 or 72, the routine is ended at 74.

Operation of the device 10 in accordance with the flow diagram of FIG. 2 for screening, provides a good indication of whether or not a disease condition is present in the area screened, and this simplified mode of operation may be used effectively for general screening purposes.

When a lesion 14 has been identified and located by screening in accordance with this invention or by other methods and a diagnosis has been made to determine whether or not the lesion is malignant, the maximum voltage differential obtained at 64 is then used in accordance with the present invention as a prognostic indicator to help in determining optimum treatments as well as determining the scheduling of appropriate test intervals and other follow-up procedures. In patients with benign lesions, the maximum voltage differential might function as a true risk marker allowing increased monitoring of higher risk patients. Such increased monitoring is made feasible by the noninvasive test procedures of the present invention. The patient will be monitored at spaced intervals, and the maximum differential values obtained during later monitoring procedures will be compared with maximum differential values obtained earlier no identify changes in lesion cell proliferation.

Tests have been conducted where the Labeling Index obtained from a biopsy specimen has been compared with the maximum voltage differential obtained from the same lesion at 66, and it has been found that some correlation exists. As the Labeling Index increases indicating a higher level of cell proliferation, the maximum voltage differential obtained from the same lesion also increases thereby providing a corresponding indication of the proliferative rate of the lesion.

In FIG. 2, once the presence of a lesion and the indication of malignancy or nonmalignancy is obtained at 68 and 72, the maximum voltage differential is further analyzed at 74. Here the maximum voltage differential is compared with one or more reference values stored in the memory of the central control unit 44, with each of these reference values being indicative of a level of cell proliferation. Treatment levels of radiation, chemotherapy, or similar treatment for each reference level are also stored in memory, and when malignancy is indicated at 68, the treatment type and level corresponding to the reference level to which the maximum voltage differential compares at 74 is indicated at 76. Thus for more aggressive cancers identified by a greater MVD, a more aggressive treatment is indicated.

Conversely, if no malignancy is indicated at 72, stored reference levels for nonmalignant lesions are compared with the MVD at 74 to provide a true risk marker indication at 76. Thus in higher risk patients where lesion cell proliferation approaches that of a malignant lesion, frequent monitoring and more intense follow-up procedures will be indicated.

If the location of the lesion is known, it is possible to eliminate steps 66–72 of FIG. 2 and either perform steps 74 and 76 directly after step 64 or, in some instances eliminate steps 74 and 76 and provide an indication of the MVD directly on the indicator 50. Should such a direct indication be provided, then a treatment will be formulated based upon the magnitude of the indicated MVD.

Finally, rather than merely indicate treatment at 76, the central control unit 44 can be programmed to directly control a treatment device 78 based upon a stored treatment control program which is dependent upon the comparison made at 74. Thus, if the treatment device 78 is a radiotherapy unit, the intensity and duration of a radiation treatment may be directly controlled by the central control unit based upon the relationship derived at 74. The stored treatment protocol will vary as the magnitude of the MVD varies relative to a predetermined reference level or levels. During this controlled treatment, the central controller 44 is programmed to periodically obtain and indicate on the indicator 50 new MVD values during and at the termination of the treatment period so that the efficacy of the treatment can be monitored. The MVD values obtained after treatment is initiated are compared with the MVD value obtained before treatment and upon which the treatment is based, to determine the magnitude, if any, of any value differences and thus the efficacy of the treatment.

We claim:

1. A method for determining the cell proliferative rate of a lesion in a human or animal subject as a function of an electromagnetic field present in the subject, said method comprising:

detecting respective biopotentials indicative of the electromagnetic field present in said subject at each of a plurality of measurement locations located in an area of the lesion, and at least one reference location on the subject;

comparing the respective biopotentials so obtained to identify a high and low level biopotential value;

obtaining a differential value indicative of the difference between said high and low level biopotential values;

and comparing said differential value to at least one predetermined reference cell proliferation value to determine the relationship therebetween.

2. The method of claim 1 which includes taking a plurality of biopotential measurements at each said measurement location during a measurement period, obtaining an average measurement value for each said measurement location from the biopotential measurements taken from said locations during the measurement period, and comparing said average measurement values to identify therefrom said high and low level biopotential values.

3. The method of claim 2 wherein said low level biopotential value is the lowest average measurement value and said high level biopotential value is the highest average measurement value.

4. The method of claim 1 which includes initiating treatment of said lesion based upon the relationship between said differential value and said reference cell proliferation value.

5. The method of claim 4 which includes detecting biopotentials present in the area of the lesion after initiating treatment of said lesion, obtaining a differential value from said biopotentials detected after the initiation of treatment, and comparing said differential value obtained after initiating treatment with the differential value obtained before treatment to determine the efficacy of the treatment.

6. The method of claim 5 wherein obtaining the indication of the efficacy of treatment includes determining whether the magnitude of said differential value obtained after treatment is initiated differs from the differential value obtained before treatment.

7. The method claim 4 which includes directly controlling said treatment in response to the magnitude of said differential value.

* * * * *